(12) United States Patent
Rauter

(10) Patent No.: US 9,791,715 B2
(45) Date of Patent: Oct. 17, 2017

(54) VIEW PANEL FOR GOGGLES OR HELMET VISOR

(71) Applicant: Christoph Rauter, Vienna (AT)

(72) Inventor: Christoph Rauter, Vienna (AT)

( * ) Notice: Subject to any disclaimer, the term of this patent is extended or adjusted under 35 U.S.C. 154(b) by 84 days.

(21) Appl. No.: 14/780,413

(22) PCT Filed: Jan. 15, 2014

(86) PCT No.: PCT/EP2014/050718
§ 371 (c)(1),
(2) Date: Sep. 25, 2015

(87) PCT Pub. No.: WO2014/154370
PCT Pub. Date: Oct. 2, 2014

(65) Prior Publication Data
US 2016/0054582 A1   Feb. 25, 2016

(30) Foreign Application Priority Data

Mar. 26, 2013 (AT) .............................. A 50207/2013

(51) Int. Cl.
| | |
|---|---|
| *G02C 1/00* | (2006.01) |
| *G02C 3/02* | (2006.01) |
| *A61F 9/02* | (2006.01) |
| *G02C 9/04* | (2006.01) |
| *G02B 1/18* | (2015.01) |
| *A42B 3/22* | (2006.01) |
| *G02C 7/02* | (2006.01) |
| *G02C 7/10* | (2006.01) |

(52) U.S. Cl.
CPC .................. *G02C 3/02* (2013.01); *A42B 3/22* (2013.01); *A61F 9/02* (2013.01); *G02B 1/18* (2015.01); *G02C 7/02* (2013.01); *G02C 7/10* (2013.01); *G02C 9/04* (2013.01); *A61F 2009/021* (2013.01)

(58) Field of Classification Search
CPC .................................... G02C 11/08; G02C 1/00
USPC .......................... 351/43, 41; 2/426, 428, 429
See application file for complete search history.

(56) References Cited

U.S. PATENT DOCUMENTS

| | | | |
|---|---|---|---|
| 2,263,116 A | 11/1941 | Andrews | |
| 3,395,406 A * | 8/1968 | Smith ...................... | A61F 9/028 2/436 |
| 3,533,686 A | 10/1970 | O'Shea | |
| 5,018,223 A | 5/1991 | Dawson et al. | |
| 5,371,555 A | 12/1994 | Nagel | |
| 5,387,950 A * | 2/1995 | Weltmann ................ | G02C 5/00 2/441 |
| 6,009,564 A * | 1/2000 | Tackles .................... | A61F 9/02 2/436 |

(Continued)

FOREIGN PATENT DOCUMENTS

| | | |
|---|---|---|
| DE | 85 19 305.4 U1 | 2/1986 |
| DE | 35 23 789 A1 | 12/1986 |

(Continued)

*Primary Examiner* — Hung Dang
(74) *Attorney, Agent, or Firm* — Seed IP Law Group LLP

(57) ABSTRACT

A view panel for goggles, preferably sports goggles, ski goggles or protective goggles, or for a helmet visor, provided with at least one outer panel and at least one inner panel, wherein the outer panel is spaced apart from the inner panel and is connected to the latter by a sealant at the edges, wherein at least one optical lens is integrated in the inner panel, and goggles having such a view panel.

19 Claims, 3 Drawing Sheets

(56) References Cited

U.S. PATENT DOCUMENTS

| | | | | |
|---|---|---|---|---|
| 6,098,204 A | * | 8/2000 | Arnette | A61F 9/02 2/202 |
| 6,611,966 B1 | * | 9/2003 | Yamamoto | A61F 9/028 2/436 |
| 7,404,217 B2 | * | 7/2008 | Polinelli | A61F 9/022 2/435 |
| 2008/0170202 A1 | | 7/2008 | Wang-Lee | |

FOREIGN PATENT DOCUMENTS

| | | |
|---|---|---|
| EP | 0 338 524 B1 | 10/1989 |
| WO | 99/44555 A1 | 9/1999 |

* cited by examiner

VIEW PANEL FOR GOGGLES OR HELMET VISOR

BACKGROUND

Technical Field

The invention relates to a view panel for goggles, for example, sports goggles, ski goggles or protective goggles, or for a helmet visor, according to the preamble of claim 1 as well as goggles having such a view panel.

Description of the Related Art

A generic view panel is known from WO99/44555A. The view panel comprises an inner panel and an outer panel where the outer panel is disposed at a distance from the inner panel and is connected to this by means of an edge-side sealing means. The inner panel here designates the panel lying closer to the eyes during use and the outer panel designates the panel lying further from the eye during use. Such view panels are used for ski goggles and motor cycle helmet visors. They enable different materials to be used for the inner and the outer panels, for example, particularly scratch-resistant material for the inner panel and material which can be effectively provided with an anti-fog coating for the outer panel. Furthermore, any fogging of the panel is also counteracted by the enclosed air cushion in the intermediate space between the inner panel and the outer panel. However, these known view panels make it difficult for ametropic persons to wear optical glasses to correct the ametropia. Usually the hollow space delimited by the frame of the goggles is not sufficiently large to wear the required optical glasses under the ski goggles.

For this purpose, it is known from DE 8519305U1 to provide clamping devices within the frame of the ski goggles in which optical lenses can be clamped by means of laterally arranged support elements (so-called inner clips). The inner clips used for this purpose at the present time are inserted in the frame of the ski goggles behind the double panel.

Such optical lenses clamped in the hollow space between the face of the user and the view panel of the ski goggles are however significantly limited in their diameter compared with the optical lenses of conventional spectacles with the result that the peripheral vision is severely restricted. In addition, fogging of the optical lenses frequently occurs. Also the brushing of the user's eyelashes against the protruding optical lenses again and again poses a problem when wearing these inner clips.

BRIEF SUMMARY

It is accordingly the object of the invention to further develop a view panel of the type mentioned initially so that on the one hand it ensures advantageous usage properties and on the other hand allows the optical correction of ametropia.

This is achieved according to the invention in a view panel according to the preamble of claim 1 by the characterizing features of claim 1. In the view panel according to the invention, at least one optical lens is integrated in the inner panel for the correction of ametropia.

Unlike the optical inner clips used at the present time, the passage of light overall is influenced by only four light-refracting surfaces instead of six light-refracting surfaces. In addition, the optical lens can be anti-glare and thus the light transmission is increased or perturbing light reflections are reduced. This results in a more stress-free vision and to energy reserves in the exercise of sport. The distance of the optical lens from the eye of the user can largely be matched to the distance of "normal" optical ophthalmic lenses. Adjustment difficulties when changing between spectacles are therefore significantly reduced.

The field of view is increased significantly compared to an inner clip and the perception is improved. The usual scotoma of an inner clip is prevented and the field of view of the user is not negatively adversely affected without the additional frame. Also any slippage of the optical lens is not possible.

As a result of the larger distance of the lenses from the surface of the eye, any brushing of the eyelashes against the surface of the lenses and therefore any permanent contamination is prevented. Since the optical lens is not inserted in the outer panel, a rapid disturbance as a result of environmental influences is prevented. Furthermore, as a result of the lens being integrated in the inner panel, dirt, water, dust or snow on the outer panel is not imaged in an optically distorted manner. The lens is also protected from contamination and mechanical adverse effects due to falling stones, branches or other foreign bodies.

The double panel construction affords the advantage of a high torsional rigidity. As a result of the optical lens being integrated in the double panel, large-diameter optical lenses can be integrated in the panel. The invention thus makes it possible to expand the field of view and improve the peripheral vision and contributes towards an increase in safety.

In this case, the manifestation of optical lenses comprises a transparent panel for correction of ametropias, made of any material, for example, of plastic, glass, CR-39, polycarbonate or combinations of these materials. Panels made of plastic having an index of 1.59 to 1.67, polycarbonate or Trivex are particularly suitable.

For receiving the optical lens, the inner panel can have at least one recess which allows the insertion of the lens. The lens can be glued in the recess. The recess can be stamped or milled. In the recess first fastening means can be provided for receiving the lens. The lens can have corresponding second fastening means.

According to the invention, the optical lens can be grooved and be integrated in the inner panel by a tongue and groove system. In particular, it can be provided that the lens is larger than the relevant recess and has a circumferential groove for insertion of at least parts of the circumferential edge of the recess so that the optical lens can be pushed into the recess.

According to the invention, it is further provided that the inner panel and the outer panel can be detachably connected to one another. As a result of the tongue and groove system and the detachable connection of the inner panel to the outer panel, it is simple to subsequently change the optical lens.

The circumferential groove can be designed as a groove milling having a width of 0.40 mm to 1.20 mm, preferably 0.80 mm and a depth of 0.20 mm to 1.00 mm, preferably 0.60 mm. The optical lens can be additionally secured in the recess by means of UV adhesive.

The groove can be designed substantially parallel to the course of that circumferential edge of the optical lens which lies in the intermediate space between inner panel and outer panel. In one embodiment, the groove can run parallel to the front surface of the lens. The optical lens should not contact the outer panel to maintain an air cushion in order to prevent fogging due to temperature differences. For this purpose, it can be provided that the lens is integrated in the inner panel in such a manner that the projection of the lens in the intermediate space between inner panel and outer panel corresponds to a maximum of half the thickness of the intermediate space. The thickness of the intermediate space can be about 3 mm to 5 mm.

The outer panel and the inner panel can be curved, and in one embodiment, is spherically curved. Accordingly, it can be provided that the front curve of the optical lens in the intermediate space between the inner panel and the outer panel runs substantially parallel to the front curves of the outer panel so that imaging errors are avoided. At the same time, the outer panels and inner panels can be shaped in such a manner that the highest possible degree of torsional rigidity of the double panel is retained.

The outer panel can comprise cellulose propionate, cellulose acetate or polycarbonate. The inner panel can comprise cellulose propionate or cellulose acetate. The panels can however also be made of other materials commonly used in ophthalmic optics. The sealant can be designed as an elastic spacing sealing element running along the edge regions of the panels, which is connected, for example, adhesively bonded to the outer panel and the inner panel. The spacing sealing element can in particular be designed as a foam sealing ring. The foam sealing ring can have a width of 3 mm to 5 mm and a thickness of 3 mm to 5 mm and be adhesively bonded to the panels by means of a double adhesive tape.

The outer panel and/or the inner panel and/or the optical lens can comprise an anti-fog coating. In particular, the inner panel and/or the optical lens can be provided on both sides with an anti-fog coating. Furthermore, the outer panel and/or the inner panel can be provided with a light-reflecting and/or infrared-radiation reflecting coating. The outer panel can have a wall thickness of 0.80 mm to 1.20 mm. The inner panel can have a wall thickness of 0.60 mm to 0.80 mm.

The view panel can be designed in such a manner that two recesses for integration of optical lenses are provided in the inner panel. Depending on the distance between the eyes (pupillary distance, the intensity of the ametropia and the type of sport or the area of application, it can be provided according to the invention that the recesses can be varied in their size and position. The minimal distance of the recesses or the optical lenses located therein can be 11 mm to 15 mm, preferably 13 mm in order to prevent a central restriction of view. The optical lenses can be designed to correct for short-sightedness, to correct for long-sightedness, as bifocal lenses or as progressive lenses.

The combining of the outer panel and inner panel to form the double panel can be accomplished by means of adhesive bonding after insertion of the optical lenses into the inner panel. For this purpose, the use of a seal in the form of a foam sealing ring which is already glued to the outer panel by means of double adhesive function is advantageous. After fabricating the inner panel with the optical lenses, after removal of the protective paper from the foam seal, this can be applied to marked places and both panels firmly adhesively bonded to one another via this foam seal.

In one embodiment, the optical lenses are prepared with a groove milling so that the inner panel can be pushed into the optical lenses. For better sealing with respect to the hollow space between the panels of the double panel, the optical lenses can be additionally secured by means of UV adhesive.

The insertion of the optical lenses results in a homogeneously closed inner panel and in the adhesively bonded state achieves the positive effects of a double panel, namely a significantly reduced probability of fogging and a high torsional rigidity. As a result of the optical lenses integrated in the double panel and the large-area contact surface in the face, a stable optical imaging without slippage is ensured.

DETAILED DESCRIPTION

Figure 1:
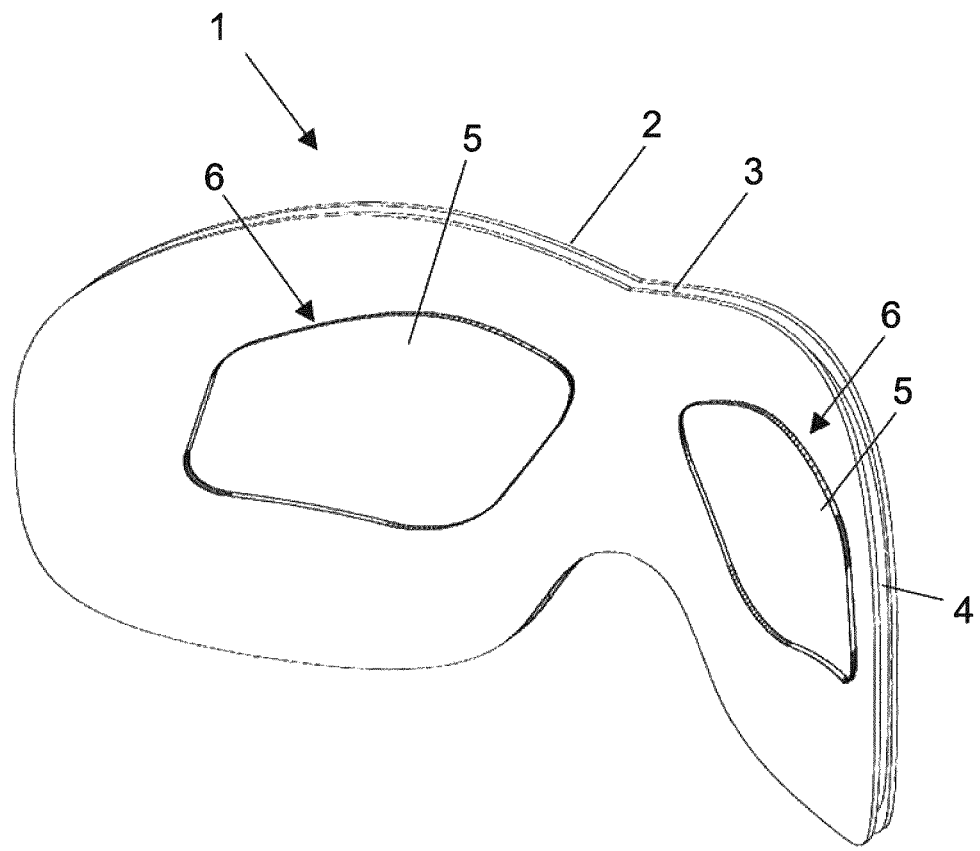
FIG 1 shows an embodiment of a view panel.

The invention is now explained with reference to exemplary embodiments which are shown schematically in the drawings.

FIG. 1 shows a first exemplary embodiment of a view panel 1 according to the invention from the view of the user. The view panel 1 comprises an outer panel 2 and an inner panel 3. A foam sealing ring 4 is disposed between the panels 2, 3. This guarantees the stability of the double panel and seals the air cushion between the panels. The inner panel 3 has two recesses 6 into which optical lenses 5 are inserted. Depending on the distance between the eyes (pupillary distance), the recess for the optical lenses can be accomplished in different panel lengths. The foam sealing ring 4 is attached in annular manner along the outer edge of the panels 2, 3 and also serves as a spacer.

As a result of the modern lens technologies available today, the front curve of the optical lens 5 (that surface which faces the outer panel 2) can be matched to the front curve of the double panels 2, 3. This avoids an flattening of the inner panel 3 which in turn could have a negative influence on the stability of the entire system and would have negative effects on the imaging effects of the optical lenses due to a changed viewing angle.

Figure 2:
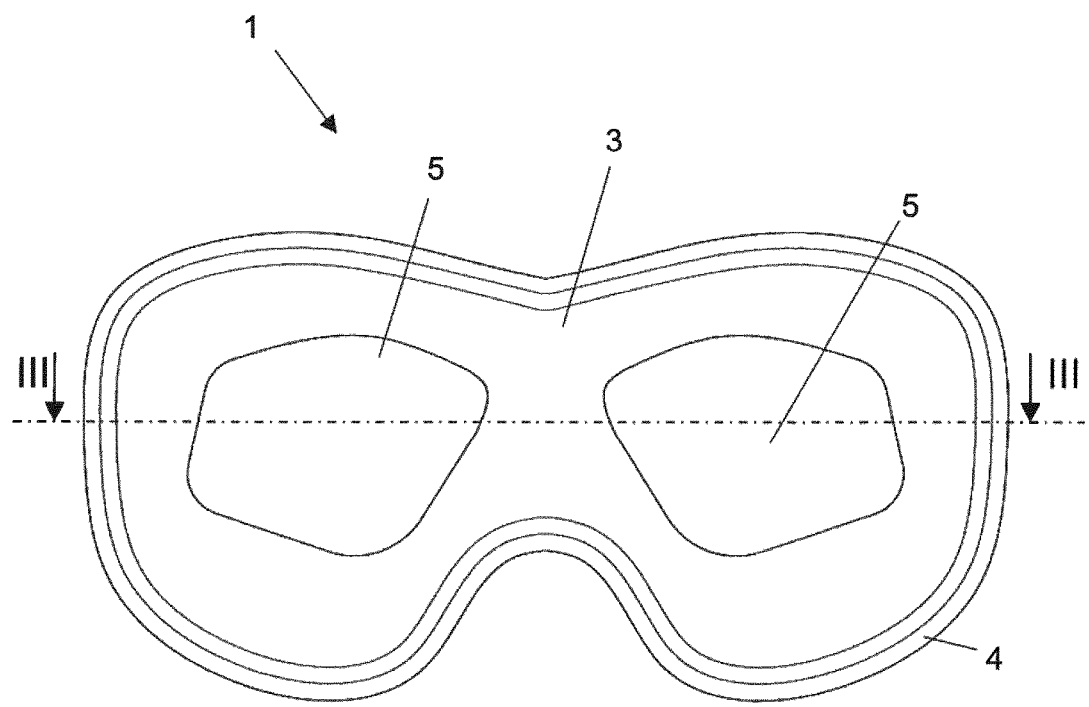
FIG. 2 shows another view of the view panel of FIG. 1.

FIG. 2 shows a further view of the view panel 1 according to the invention, where the area of the foam sealing ring 4 has been particularly identified.

Figure 3A:
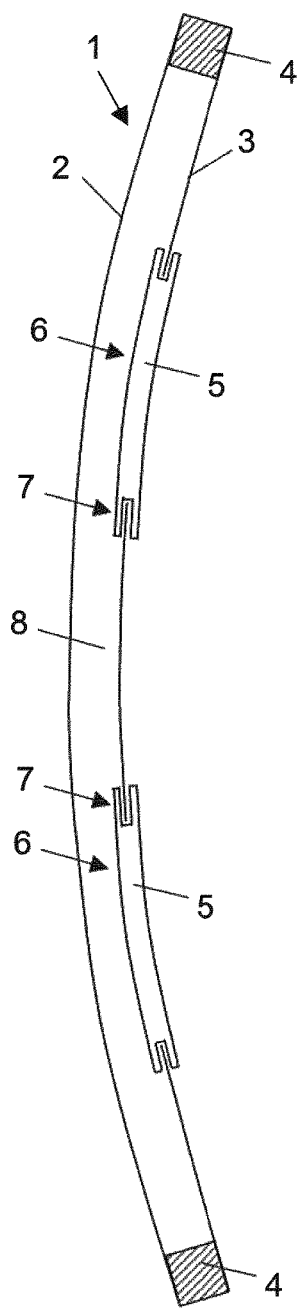
FIG. 3a-3c show other views of the view panel of FIG. 1, taken along line III-III in FIG. 2.
Figure 3B:
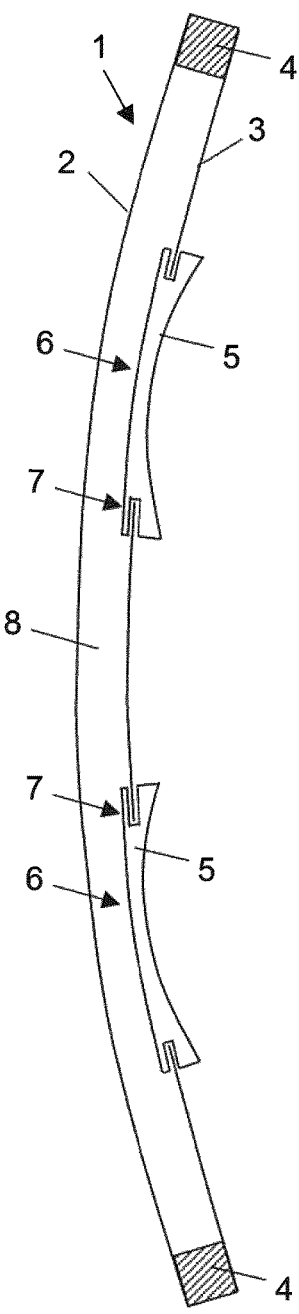
Figure 3C:
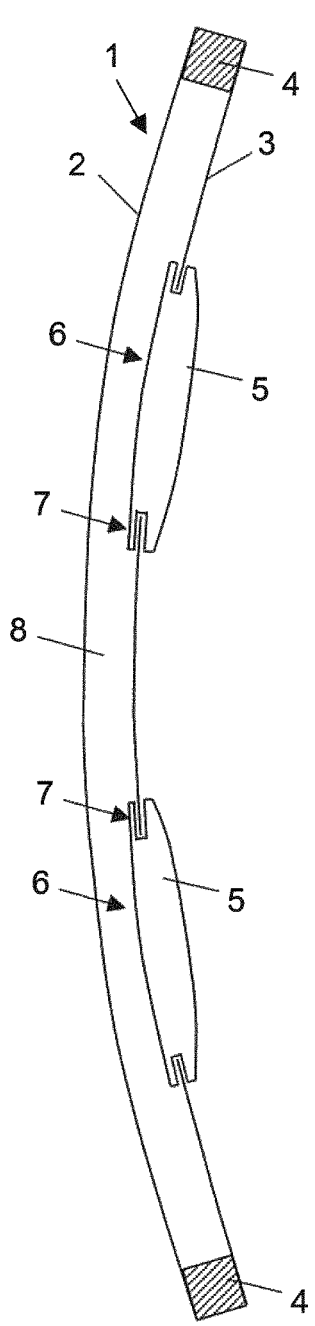

FIGS. 3a-3c show three embodiments of the view panel according to the invention along the section which is indicated in FIG. 2. The exemplary embodiments differ by the design of the optical lenses 5 which in FIG. 3a have a constant thickness, in FIG. 3b are designed as planoconcave lenses and in FIG. 3c are designed as planoconvex lenses. All the embodiments have in common that the front curve of the optical lenses 5 runs substantially parallel to the front curve of the outer panel 2 in order to avoid imaging errors.

Furthermore, in all three exemplary embodiments the optical lenses 5 are provided with a circumferential groove 7 into which the edge of the recess 6 of the inner panel 3 engages in order to keep the lenses 5 in the recesses 6. The groove 7 is provided substantially in the central region of the lenses 5 in order to achieve that the penetration of the lenses 5 into the intermediate space 8 between inner panel 3 and outer panel 2 corresponds to a maximum of approximately half the thickness of the intermediate space 8.

The invention is not restricted to the exemplary embodiments shown but covers further exemplary embodiments within the framework of the protective claims. The invention covers in particular goggles, for example, ski goggles, sports goggles or protective goggles or helmet visors, as well as protective helmets for police or military use, as well as fire brigade helmets comprising a view panel according to the invention.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A view panel for goggles, sports goggles, ski goggles or protective goggles, or for a helmet visor, comprising:
    at least one outer panel and at least one inner panel, wherein the outer panel is spaced apart from the inner panel and the outer panel is connected to the inner panel by a sealant at edge regions of the outer panel and the inner panel, at least one optical lens being integrated in the inner panel, the optical lens being either a converging lens or a diverging lens, wherein a curved front surface of the optical lens is between the inner panel and the outer panel and is parallel to a curved front surface of the outer panel.

2. The view panel according to claim 1 wherein, the inner panel has at least one recess for receiving the optical lens.

3. The view panel according to claim 2 wherein the optical lens is glued in the recess.

4. The view panel according to claim 2 wherein the optical lens has a circumferential groove for insertion of at least parts of the circumferential edge of the recess so that the optical lens can be pushed into the recess.

5. The view panel according to claim 4 wherein the circumferential groove is designed as a groove milling having a width of 0.40 mm to 1.20 mm and a depth of 0.20 mm to 1.00 mm.

6. The view panel according to claim 4 wherein the optical lens is additionally secured in the recess by means of a UV adhesive.

7. The view panel according to claim 4 wherein the groove is designed substantially parallel to the course of that circumferential edge of the optical lens which lies in the intermediate space between inner panel and outer panel.

8. The view panel according to claim 1 wherein the optical lens is integrated in the inner panel in such a manner that the extent of the projection of the optical lens in the intermediate space between the inner panel and the outer panel corresponds to a maximum of half the thickness of the intermediate space.

9. The view panel according to claim 1 wherein the sealant is designed as an elastic spacing sealing element running along the edge regions of the panels, which is adhesively bonded to the outer panel and the inner panel.

10. The view panel according to claim 9 wherein the spacing sealing element is designed as a foam sealing ring.

11. The view panel according to claim 10 wherein the foam sealing ring has a width of 3 mm to 5 mm and a thickness of 3 mm to 5 mm and is adhesively bonded to the panels by means of a double adhesive tape.

12. The view panel according to claim 1 wherein the outer panel and/or the inner panel and/or the optical lens comprise an anti-fog coating.

13. The view panel according to claim 12 wherein the inner panel and/or the optical lens is provided on both sides with an anti-fog coating.

14. The view panel according to claim 1 wherein the outer panel and/or the inner panel is provided with a light-reflecting and/or infrared-radiation reflecting coating.

15. The view panel according to claim 1 wherein two recesses for integration of optical lenses are provided in the inner panel.

16. The view panel according to claim 15 wherein the minimal distance of the optical lenses from one another is 11 mm to 15 mm.

17. The view panel according to claim 1 wherein the optical lenses are designed to correct for short-sightedness, to correct for long-sightedness, as bifocal lenses or as progressive lenses.

18. Goggles, preferably sports goggles, ski goggles or protective goggles or visor of a helmet, in particular visor for fire brigade helmets or police or military protective helmets comprising a view panel according to claim 1.

19. A helmet having a helmet visor according to claim 18.

* * * * *